US010031123B2

(12) United States Patent
Zarnescu et al.

(10) Patent No.: US 10,031,123 B2
(45) Date of Patent: Jul. 24, 2018

(54) MECHANICAL BIOMARKERS FOR OOCYTE AND EMBRYO VIABILITY

(71) Applicant: The Board of Trustees of the Leland Stanford Junior University, Stanford, CA (US)

(72) Inventors: Livia Zarnescu, Palo Alto, CA (US); David B. Camarillo, Aptos, CA (US); Jinnuo Han, Mountain View, CA (US); Renee A. Reijo Pera, Los Altos, CA (US); Shawn L. Chavez, Fremont, CA (US); Barry Behr, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/919,445

(22) Filed: Oct. 21, 2015

(65) Prior Publication Data
US 2016/0109428 A1    Apr. 21, 2016

Related U.S. Application Data

(63) Continuation of application No. 13/739,965, filed on Jan. 11, 2013, now Pat. No. 9,179,935.
(Continued)

(51) Int. Cl.
*G01N 33/483* (2006.01)
*A61B 17/435* (2006.01)
(Continued)

(52) U.S. Cl.
CPC ....... *G01N 33/4833* (2013.01); *A61B 17/435* (2013.01); *C12M 21/06* (2013.01);
(Continued)

(58) Field of Classification Search
CPC .... G01N 33/689; A61B 17/435; C12M 41/46; C12M 35/04; C12M 21/06
(Continued)

(56) References Cited

U.S. PATENT DOCUMENTS 6,489,135 B1   12/2002  Parrott
6,593,139 B1*   7/2003  Yanagimachi ..... C07K 14/4705
                                                    435/325

(Continued)

OTHER PUBLICATIONS

Alteration in the Mechanical Properties of Human Ovum Zona Pellucida Following Fertilization: Experimental and Analytical Studies. Experimental Mechanics, Feb. 2011, vol. 51, Issue 2, pp. 175-182, Published Online. Apr. 15, 2010.*

(Continued)

*Primary Examiner* — Navin Natnithithadha
*Assistant Examiner* — Sunita Reddy
(74) *Attorney, Agent, or Firm* — Foley & Lardner LLP; Cliff Z. Liu

(57) ABSTRACT

Provided are methods for the determination of the viability of a mammalian embryo or a potential embryo generated from a mammalian oocyte, comprising applying a mechanical stimulus to the embryo or oocyte, detecting a temporal response of the embryo or oocyte to the mechanical stimulus, and deriving measurements for one or more parameters from the temporal response, the measurements being indicative of viability. Also provided are methods for selecting an embryo for transfer and methods for enhancing the viability of an embryo or oocyte.

18 Claims, 15 Drawing Sheets

Related U.S. Application Data

(60) Provisional application No. 61/586,561, filed on Jan. 13, 2012.

(51) Int. Cl.
    *G01N 33/68* (2006.01)
    *C12M 3/00* (2006.01)
    *C12M 1/42* (2006.01)
    *C12M 1/34* (2006.01)

(52) U.S. Cl.
    CPC ............ *C12M 35/04* (2013.01); *C12M 41/46* (2013.01); *G01N 33/689* (2013.01); *G01N 33/483* (2013.01)

(58) Field of Classification Search
    USPC ............. 600/33–35; 435/29, 2; 128/897–899
    See application file for complete search history.

(56) References Cited

U.S. PATENT DOCUMENTS

| | | | |
|---|---|---|---|
| 6,641,526 B1 * | 11/2003 | Wakayama | A01N 1/0284 424/561 |
| 6,695,765 B1 | 2/2004 | Beebe et al. | |
| 7,531,715 B1 * | 5/2009 | Campbell | A01K 67/0273 435/325 |
| 7,963,906 B2 | 6/2011 | Wong et al. | |
| 7,981,399 B2 | 7/2011 | Burns | |
| 8,026,065 B2 | 9/2011 | Wells et al. | |
| 8,497,119 B1 * | 7/2013 | Taylor | C12N 5/0609 435/287.3 |
| 2007/0087321 A1 * | 4/2007 | Pribenszky | A01N 1/0289 435/1.1 |
| 2010/0240132 A1 * | 9/2010 | Lanza | A01K 67/0273 435/455 |
| 2013/0117870 A1 * | 5/2013 | Fahrenkrug | C12N 15/8509 800/14 |

OTHER PUBLICATIONS

Francesco Mainardi and Giorgio Spada; Creep, Relaxation and Viscosity Properties for Basic Fractional Models in Rheology; The European Physical Journal, Special Topics, vol. 193 (2011) 133-160 (attached).*
Behr et al. "Preliminary clinical experience with human blastocyst development in vitro without co-culture," Human Reproduction 14:454-457 (1998).
Cha et al. "Maturation in vitro of immature human oocytes for clinical use," Human Reproduction Update 4:103-120 (1998).
Eppig et al. "Relationship between the developmental programs controlling nuclear and cytoplasmic maturation of mouse oocytes," Developmental Biology 164:1-9 (1994).
Gardner et al., "Culture and transfer of human blastocysts increases implantation rates and reduces the need for multiple embryo transfers," Fertil Steril 69:84-88 (1998).
Guilak et al. "Viscoelastic Properties of the Cell Nucleus," Biochemical and Biophysical Research Communications 269:781-786 (2000).
Izadyar et al. "The promotory effect of growth hormone on the developmental competence of in vitro matured bovine oocytes is due to improved cytoplasmic maturation," Molecular Reproduction and Development 49:444-453 (1998).
Jones "Meiosis in oocytes: predisposition to aneuploidy and its increased incidence with age," Human Reproduction Update 14:143-158 (2008).
Khalilian et al. "Estimating Young's modulus of zona pellucida by micropipette aspiration in combination with theoretical models of ovum," Journal of The Royal Society 7:687-694 (2010).
Kong et al. "Comparison of open straw (OPS) vs Glass micropipette (GMP) vitrification in mouse blastocysts," Theriogenology 53:1817-1826 (2000).
Lin et al. "In situ mechanical characterization of mouse oocytes using a cell holding device", Lab on a Chip, 10:2154-2161 (2010).
Liu et al. "Changes in the distribution of mitochondria before and after in vitro maturation of human oocytes and the effect of in vitro maturation on mitochondria distribution," Fertil Steril 93:1550-1555 (2010).
Liu et al. "In-situ Mechanical Characterization of Mouse Oocytes Using a Cell Holding Device," 2010 IEEE 23rd International Conference on Micro Electro Mechanical Systems (MEMS):947-950.
Marteil et al. "Role of oocyte quality in meiotic maturation and embryonic development," Reproductive Biology 9:203-224 (2009).
Mohr et al. "The use of fluorescein diacetate to assess embryo viability in the mouse," Journal of Reproduction and Fertility, 58(1):189-196 (1980).
Moor et al. "Oocyte maturation and embryonic failure," Human Reproduction Update 4:223-236 (1998).
Murayama et al. "Elasticity measurement of zona pellucida using a micro tactile sensor to evaluate embryo quality," Journal of Mammalian Ova Research 25:8-16 (2008).
Murayama et al. "Micro-mechanical Sensing Platform for the Characterization of the Elastic Properties of the Ovum Via Uniaxial Measurement," J. Biomechanics 37:67-72 (2004).
Murayama et al. "Mouse zona pellucida dynamically changes its elasticity during oocyte maturation, fertilization, and early embryo development," Human Cell 19:119-125, (2006).
Pajerowski et al. "Physical plasticity of the nucleus in stem cell differentiation," Proc. Natl. Acad. Sci. 104(40):15619-15624 (2007).
Pajerowski et al. "Physical plasticity of the nucleus in stem cell differentiation," Proceedings of the National Academy of Sciences 104(40):15619-15624 (2007).
Sun et al. "Mechanical Property Characterization of Mouse Zona Pellucida," IEEE Transactions of Nanobioscience 2:279-286 (2003).
Vaziri et al. "Mechanics and deformation of the nucleus in micropipette aspiration experiment," Journal of Biomechanics 40(9):2053-2062 (2007).
Wells et al. "Gene expression profiling of human oocytes at different maturational stages and after in vitro maturation," American Journal of Obstetrics and Gynecology 198:455.e1-455.e9 (2008).
Zuccotti et al. "Maternal Oct-4 is a potential key regulator of the developmental competence of mouse oocytes," BMC Developmental Biology 8:97-110 (2008).
International Search Report for International Application No. PCT/US2013/021292, dated Apr. 29, 2013.
Extended European Search Report for European Application No. 13736056.6, dated Aug. 11, 2015.
Non-Final Office Action for U.S. Appl. No. 13/739,965, dated Oct. 31, 2014.
Final Office Action for U.S. Appl. No. 13/739,965, dated Mar. 12, 2015.
Notice of Allowance for U.S. Appl. No. 13/739,965, dated Jul. 1, 2015.

* cited by examiner

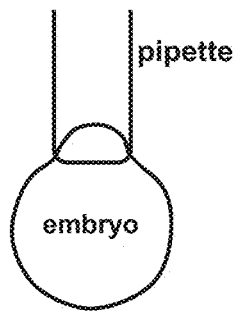
FIG. 5A
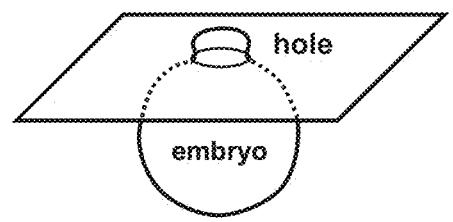
FIG. 5B
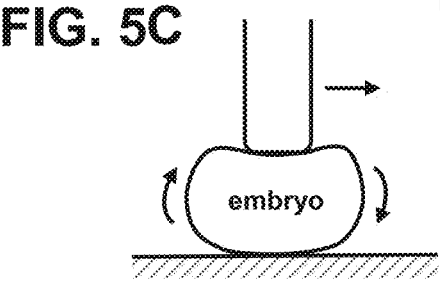
FIG. 5C
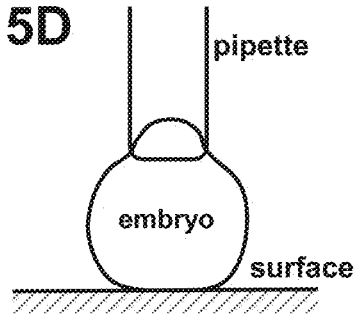
FIG. 5D
FIG. 5E
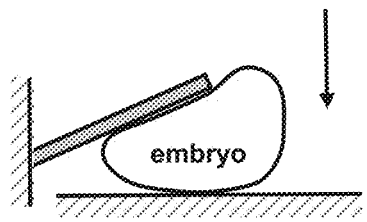
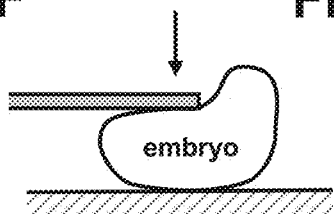
FIG. 5F
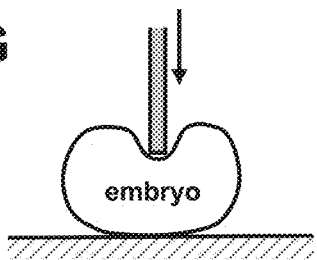
FIG. 5G

MECHANICAL BIOMARKERS FOR OOCYTE AND EMBRYO VIABILITY

CROSS REFERENCE TO RELATED APPLICATIONS

This application is a continuation of U.S. application Ser. No. 13/739,965, filed Jan. 11, 2013, which in turn claims the benefit under 35 U.S.C. § 119(e) of U.S. Provisional Application Ser. No. 61/586,561, filed Jan. 13, 2012, each of which is incorporated by reference in its entirety.

FIELD OF THE DISCLOSURE

The present disclosure, in general, relates to methods for providing measurements for the determination of the development potential (e.g., viability) of a mammalian embryo or a potential embryo generated from a mammalian oocyte. Also provided are methods for selecting an embryo for transfer for in vitro fertilization (IVF) and methods for enhancing the viability of an embryo or oocyte.

BACKGROUND

The following discussion of the background of the disclosure is merely provided to aid the reader in understanding the disclosure and is not admitted to describe or constitute prior art to the present disclosure.

Nearly 1 out of 6 couples in the U.S. seeking to have children experience infertility. For those who have been unsuccessful conceiving a child with the aid of pharmaceuticals, surgery, or artificial insemination, in vitro fertilization (IVF) is their best option to finally become pregnant. However, the average live-birth rate for an IVF cycle is approximately 1-in-3 and this rate has only modestly increased since the advent of IVF more than 30 years ago.

An IVF cycle consists of hormonal stimulation so that several eggs can be surgically harvested, and then these ova are fertilized in vitro so that they can develop in culture for evaluation. Typically after three days, the embryos are examined under the microscope by the embryologist to select the most viable embryos to transfer back to the mother. The embryologist faces a significant dilemma where he or she must select which of these available embryos is viable, based on morphological assessment.

Ideally, only one embryo should be transferred back to the mother to eliminate the risks associated with multiple gestation pregnancies such as pre-term birth, low birth weight, and the necessity for fetal reduction in some cases. Due to the subjective and inaccurate nature of this morphological assessment, however, multiple embryos are transferred back to the mother in 90% of cases in order to increase the chances for a successful implantation.

Another IVF technique extends the length of embryo culture to five days which is the blastocyst stage (Behr et al., *Human Reproduction*, 14(2):454-7, 1999). The embryos that survive to the blastocyst stage are thought to be more viable and therefore have a higher rate of implantation. Culturing to the day-five blastocyst stage has been used clinically to transfer fewer embryos but has also demonstrated how poor the more common day-three selection is in predicting survival.

Moreover, unfortunately, not all women qualify for blastocyst transfer because they may not have a sufficient number of embryos at day-three to risk further attrition. Even for those who do qualify, blastocyst transfer is still controversial as some propose that embryos should be transferred earlier to avoid undue stress on the embryos. Therefore, embryologists need an objective and quantitative measure of embryo viability at an early stage to improve a patient's chance of achieving a single live-birth.

SUMMARY

The present disclosure provides, in one embodiment, a method for determination of the viability of a mammalian embryo or a potential embryo generated from a mammalian oocyte, comprising applying a mechanical stimulus to the embryo or oocyte; detecting a temporal response of the embryo or oocyte to the mechanical stimulus; and deriving measurements for one or more parameters from the temporal response, the measurements being indicative of viability.

In some aspects, the mechanical stimulus comprises a negative, substantially constant, pressure on a portion of the surface of the embryo or oocyte, for a period of time sufficient to inflate the embryo or oocyte at the portion but not to damage the embryo or oocyte.

In one aspect, the one or more parameters comprise at least one of speed and depth of inflation.

In one aspect, the method further comprises comparing the measurements to those measured for a reference embryo or oocyte under similar conditions. In some aspects, the reference embryo or oocyte is a virtual embryo or oocyte generated by pooling measurement data from a reference population of embryos or oocytes, or an embryo or oocyte from the same mammalian donor as the embryo or oocyte being measured. In some aspects, the method further comprises determining that the embryo is more likely viable, or the oocyte is more likely to generate a viable embryo, than the reference embryo or oocyte, if the measured speed is lower than that of the reference embryo or oocyte, or if the measured depth is shorter than that of the reference embryo or oocyte.

In one aspect, the speed comprises an initial inflation speed defined as a ratio of depth of inflation to length of time starting from the beginning of application of the negative pressure. In some aspects, the length of time is less than about 0.5 second.

In another aspect, the depth comprises the depth of inflation during a period after an initial inflation slows down and substantially stabilizes. In some aspects, the period starts from at least about 0.5 second after initiation of the negative pressure and is no more than about 5 seconds.

In some aspects, the pressure is from −0.3 psi to −1 psi. In some aspects, the portion of the surface area of the embryo or oocyte is from 25 μm to 100 μm in diameter. In some aspects, the embryo is at or less than 1 day old following fertilization.

In some aspects, the embryo is a human embryo. For a human embryo, in one aspect, the portion of the surface area of the embryo or oocyte is from about 35 μm to about 65 μm in diameter. In one aspect, the pressure is from −0.35 psi to −0.75 psi.

Also provided, in another embodiment, is a method for selecting a human embryo from a plurality of embryos for transfer to a human subject, comprising applying a mechanical stimulus to each embryo or oocyte of the plurality; detecting a temporal response of each embryo or oocyte to the mechanical stimulus; deriving measurements for one or more parameters from the temporal response, the measurements being indicative of viability; and selecting an embryo from the plurality of embryos for the transfer based on the measurements.

Another embodiment provides a method for tuning an embryo or oocyte, comprising applying a negative, substantially constant, pressure on a portion of the surface of the embryo or oocyte, for a period of time sufficient to inflate the embryo or oocyte at the portion but not to damage the embryo or oocyte. In one aspect, the embryo is a human embryo that is less than 3 days old following fertilization. In one aspect, the portion of the surface area of the embryo or oocyte is from 40 µm to 60 µm and the pressure is from −0.3 psi to −0.5 psi.

BRIEF DESCRIPTION OF THE DRAWINGS

Provided as embodiments of this disclosure are drawings which illustrate by exemplification only, and not limitation, wherein:

FIG. 5A, FIG. 5B, FIG. 5C, FIG. 5D, FIG. 5E, FIG. 5F, and FIG. 5G illustrate different ways to apply a mechanical stimulus to an embryo or oocyte;

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

The following examples serve to illustrate the present disclosure. These examples are in no way intended to limit the scope of the disclosure.

A quantitative and non-invasive predictor of viability has been developed for oocytes and embryos that entails mechanical stimuli. The viability test is shown to be effective at as early as day 1 after fertilization, as well as in oocytes prior to fertilization. The early viability test can help predict which embryos would have survived to the blastocyst stage without having to keep them in a stressful culture environment for several days for further viability evaluation.

Surprisingly, the mechanical stimuli employed in this viability test have been shown to increase embryo viability. Therefore, the present disclosure provides mechanical manipulation of embryos and oocytes that serve both as biomarkers for viability testing and as a mechanism to improve their viability.

Figure 1:
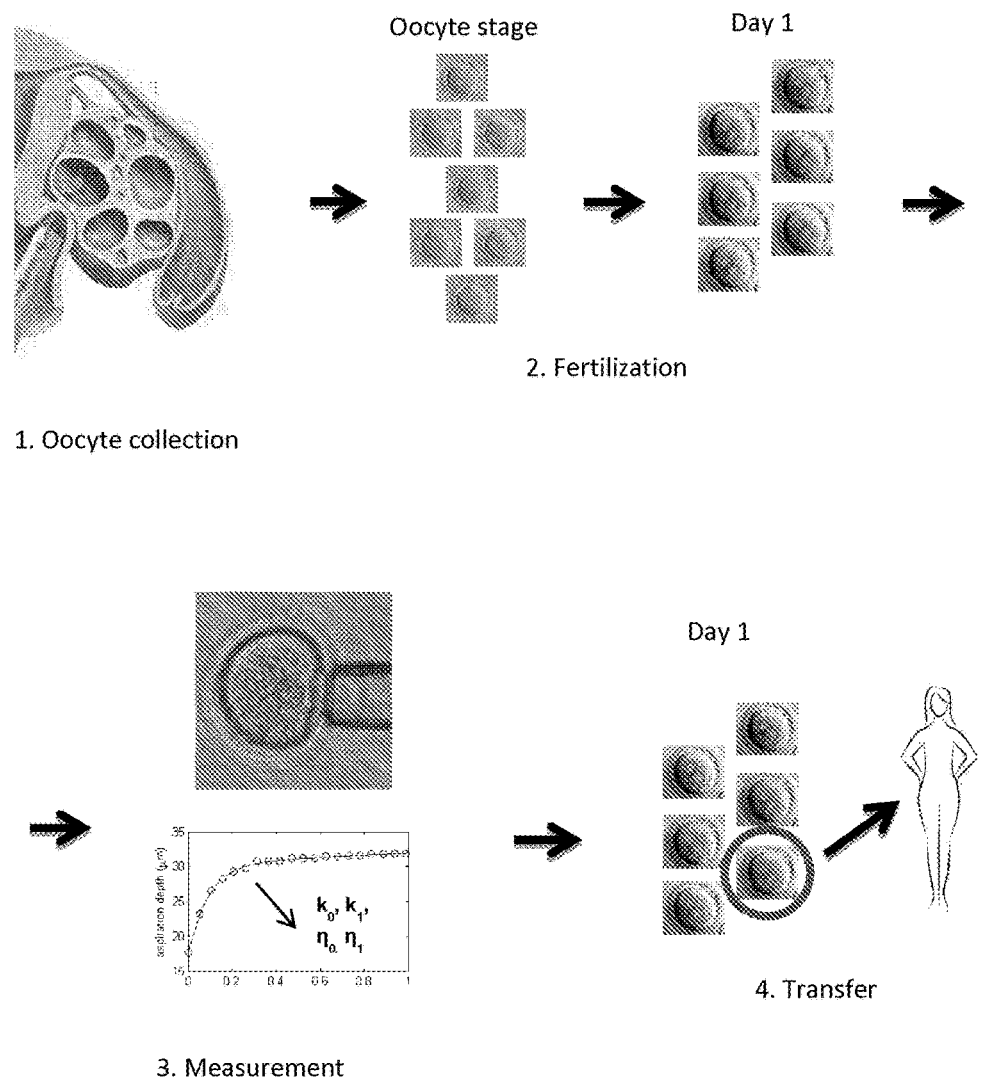
FIG. 1 illustrates an improved IVF procedure taking advantage of the present technology.

With the presently disclosed devices and methods, an improved IVF procedure can be achieved, as illustrated in FIG. 1. Upon retrieval from the follicles in the mother, oocytes are incubated under suitable condition to allow fertilization. Then, after fertilization, even immediately after fertilization, mechanical stimulus is applied to each of the fertilized embryos (FIG. 1, step 3), at which step a temporal response is detected. Subsequently, certain measurements are derived from the detected temporal response, with appropriate mathematical transformation as applicable. Based on such measurements, which reflect the viability of the embryos, the embryo with the predicted highest viability is selected and transferred to a carrier within the same day (FIG. 1, step 4), such as the oocyte donor, to proceed for further embryonic development.

Temporal Response and Derived Measurements

The mechanical stimuli employed in various aspects of the present disclosure can allow measuring of mechanical properties of several different bodies and parts thereof, including the entire embryo body, the zona pellucida, the cytoplasm or the embryo, cortical granules, blastomeres, the cytoplasm of each blastomere, the individual organelles of each blastomere including the nucleus, nucleoli, mitochondria, endoplasmic reticulum, and cytoskeleton, as well as any cellular fragments or extracellular matrix present between the blastomeres or other cellular features such as plaques/boli.

Detailed physical parameters to be measured include, without limitation, size, mass, density, viscosity, internal pressure, elasticity, response time, recoil, complex impedance, frequency response, hysteresis, plasticity, and creep. Surface properties such as static friction, dynamic friction, membrane thickness over time, roughness, and texture can be obtained. When measuring elasticity, one can look at parameters such as elastic modulus, shear modulus, and general stiffness in each of the 6 degrees of freedom including compression, expansion, and torsion.

In some aspects, mechanical stimuli are employed to trigger deformation or movement of an embryo or oocyte so that a temporal response can be measured. In general, the temporal response can be recorded as geometric change over time and can reflect the stiffness and/or viscosity of the embryo or oocyte. In some aspects, embryos and oocytes with relatively higher stiffness and viscosity are more likely viable.

Figure 2A:
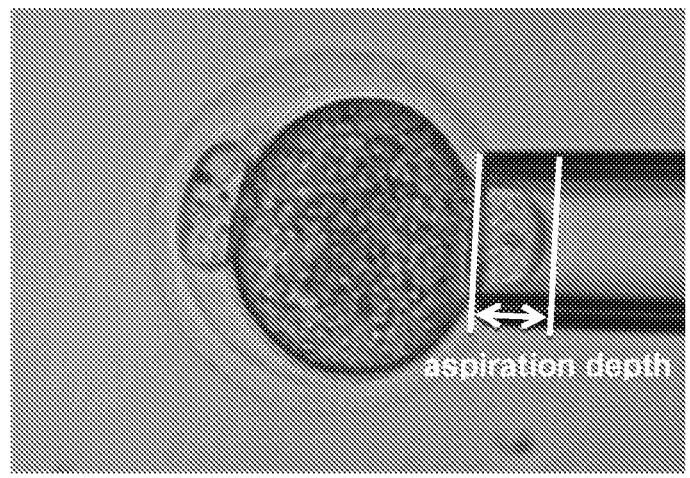
FIG. 2A and FIG. 2B show two microscope images illustrating the difference, as determined by the present technology, between viable and non-viable embryos.
Figure 2B:
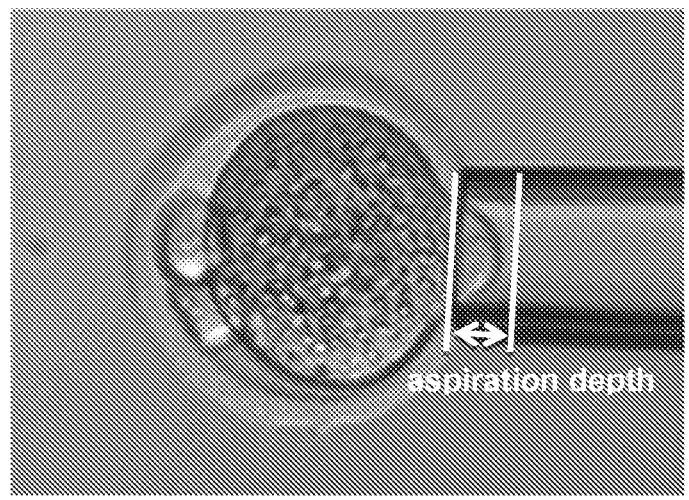

For instance, FIGS. 2A and 2B illustrate the inflation of a portion of an embryo under a negative air pressure provided by a pipette that draws the portion into the pipette. Within a certain time period, the embryo in FIG. 2A exhibits a relatively larger inflation (i.e., greater aspiration depth) as compared to that in FIG. 2B. Accordingly, the embryo of FIG. 2B can be predicted to be more likely viable than the embryo of FIG. 2A which was confirmed with experimental data.

Figure 3A:
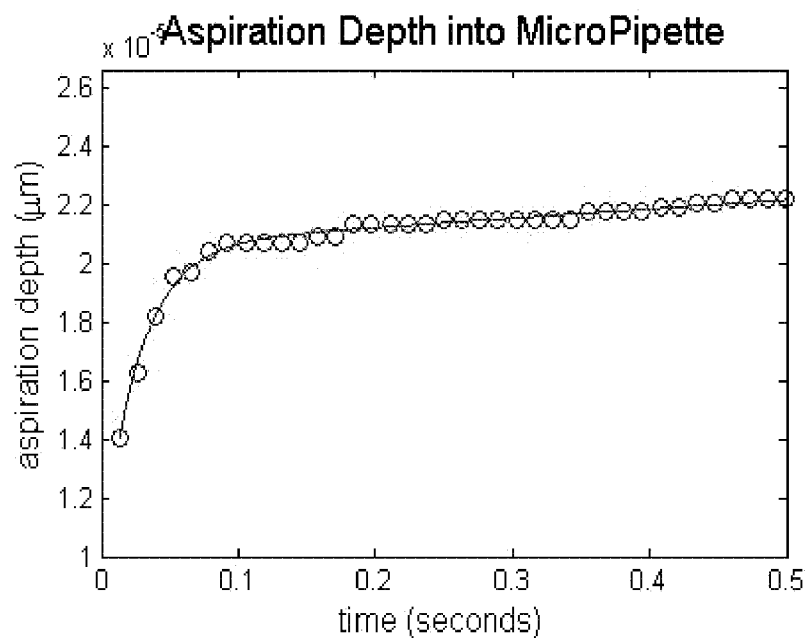
FIG. 3A shows an aspiration curve created with data observed in a temporal response of an embryo upon application of a mechanical stimulus.
Figure 3B:
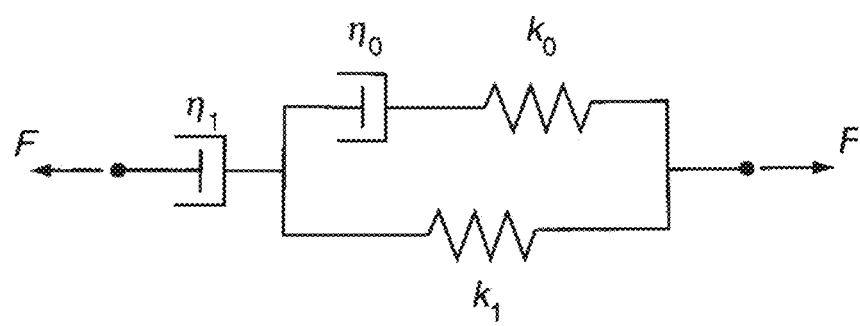
FIG. 3B shows a linear elastic solid model used to fit the data in FIG. 3A.

The temporal response of an embryo or oocyte can be represented as a geometric change over time curve, as illustrated in FIG. 3A. In FIG. 3A, the x-axis is time and the y-axis, in this particular example, is aspiration depth. Such a curve can then be fitted into a linear elastic solid model, such as one shown in FIG. 3B. The linear elastic solid model, also referred to as the Zener model, is a method of modeling the behavior of a viscoelastic material using a linear combination of springs and dashpots to represent elastic and viscous components, respectively.

The linear elastic solid model can be represented with the following equations:

$$\text{depth} = F_0 \left[ \frac{1}{k_1} \left( 1 - \frac{k_0}{k_0 - k_1} e^{-t/\tau} \right) - \frac{t}{\eta_1} \right], \text{where} \quad (A)$$

$$\tau = \eta_0 \left( \frac{k_0 + k_1}{k_0 k_1} \right). \quad (B)$$

All parameters, $k_0$, $k_1$, $\tau$ (or $\eta_0$) and $\eta_1$, can be determined by fitting the aspiration depth to the equation above. $F_0$ is defined as the applied pressure divided by the area of the pipette opening. Here, the behavior of an embryo or oocyte is modeled as a combination of solid-like ($k_0$, $k_1$) and liquid-like behavior ($\eta_0$ and $\eta_1$). Therefore, this model allows measurement of both kinds of behavior.

The parameter $k_0$, together with $k_1$, describe the "instant elongation" experienced by the embryo or oocyte upon application of a mechanical stimulus. This instant elongation is $1/(k_0+k_1)$ as seen in the graph of FIG. 4, and can be viewed as a measure of the "slack" in the elastic elements of the embryo or oocyte, or the amount of force that can be applied on it before a marked resistance is exhibited.

The parameter $k_1$ can be viewed as a general measure of stiffness, and may represent how tightly the proteins in the cell membrane or zona pellucida are crosslinked.

Figure 4:
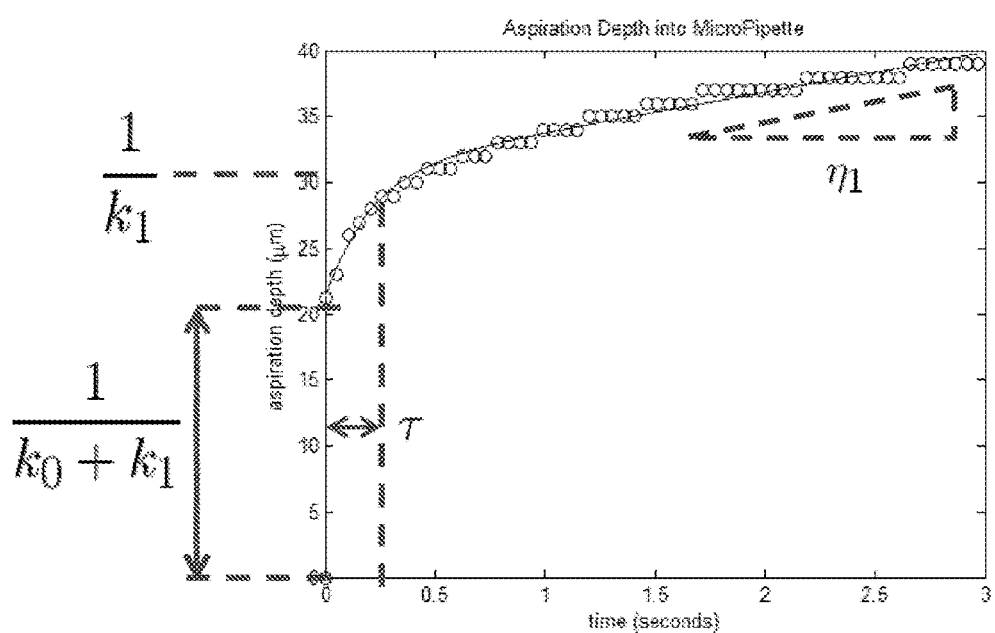
FIG. 4 shows how each parameter in a linear elastic solid model can be interpreted, mechanically and how the mechanical parameters are reflected in the aspiration curves.

The parameter $\eta_1$ can be viewed as a measure of how much the zona pellucida and cell inside continue to deform in response to the stimulus (FIG. 4). Like in the linear elastic solid model, after the spring elements have fully extended, this parameter is responsible for whatever shape changes at the molecular level keep the embryo elongating.

The parameter $\tau$ represents how fast (e.g., speed) the embryo or oocyte deforms (e.g., enters the pipette) after the initial instant elongation (FIG. 4), and can be viewed as a measure of the viscosity of the cytoplasm or the fluid in the space between the zona pellucida and the cell inside.

The data presented in the experimental example shows that all of these parameters, in particular $k_1$, $\tau$ and $\eta_1$ and combinations thereof are good predicators for the viability of embryos and oocytes.

Mechanical Stimuli

FIG. 2A-2B and FIG. 5A illustrate one form of mechanical stimulus that can be applied to an embryo or oocyte for the purpose of viability prediction and/or enhancement. Here, a negative air pressure (e.g., a lower pressure inside the pipette relative to the pressure inside the embryo or oocyte outside the pipette) is applied to a portion of the embryo or oocyte surface so that that portion inflates into the pipette.

Many other types of mechanical stimuli are also suitable, however. A few non-limiting examples are illustrated in FIG. 5B-G. Mechanical stimuli can be applied with a needle, or a micropipette, which can be used to cause either negative or positive pressure (aspiration or ejection, respectively) in order to deform, hold, or otherwise perturb the zona pellucida, cytoplasm, or other contents of an embryo or oocyte near its surface.

Negative or positive pressure can also be applied by another entity, such as the petri dish holding the embryo, or a pressure impulse can be used, similar to a glaucoma test. An embryo or oocyte can also be squashed by a flat sheet with a hole in it and the deformation of the membrane and cytoplasm over time can be measured either while holding the sheet steady, or dithering it in various ways (FIG. 5B).

Alternatively, a solid object can be pressed upon one side of the embryo or oocyte against a flat supporting surface, thereby generating a shear pressure by moving horizontally (FIG. 5C). The object here can have a variety of shapes ranging from flat and wide to narrow and rod-like.

The embryo or oocyte can be held still by a micropipette while being dragged along a surface that can be either smooth or with varying degrees of roughness (FIG. 5D). Such a surface can then provide a pressure to push the embryo or oocyte into the pipette. Additionally an ultrasound transducer can be used to send a pressure wave to perturb the embryo or its contents.

In another embodiment, a flexible cantilever or array of cantilevers of arbitrary shape can be used to push the embryo or oocyte against a surface, and both the deformation of the embryo's membrane/contents as well as the cantilever's own deformation can be measured (FIG. 5E, arrow showing direction of pushing). This will allow one to determine the force exerted by the embryo on the cantilever. If the stiffness of various components inside the embryo as well as their configuration relative to each other can be properly measured, the contribution of each component to the force exerted back on the cantilever can then be determined (e.g., stiffer objects will contribute more).

A similar configuration involves a flexible pipette or pillar where it is pushed either longitudinally or axially into an embryo or oocyte, and its deflection (FIG. 5F) or compression is measured (FIG. 5G).

Optical pressure can also be exerted on various components inside the embryo or on the embryo itself by focusing a beam of light in order to cause a force near its focal point (an optical trap). This will allow one to exert forces originating inside the embryo instead of just at its surface as with a micropipette, while still remaining non-invasive. Microbeads could also be inserted into the embryo or into the individual blastomeres, and an optical trap can be used to drag them around and push on various objects.

In some aspects, one can also conduct inertial measurements on an embryo or oocyte by accelerating, bouncing, or rotating the well containing it and observing the movements of its contents relative to each other. Applying hydrostatic pressure to a well or container with an embryo in it or placing an embryo in a microfluidic channel while observing the embryo's shape or position over time can yield mechanical information. The embryo can also be stretched by using micropipettes at both ends to pull on it, or individual components inside it can be pulled apart using two optical traps to yield information about its stiffness at various spatial locations. Ballistic testing can also be conducted by launching microbeads at the embryo and observing membrane deformation over time. All of the actions described herein can alternatively be applied cyclically to measure hysteresis or a loss coefficient over time, without limitation.

Tuning of Mechanical Stimuli

It is contemplated that the mechanical stimuli can to be applied appropriately with suitable magnitude to provoke a suitable temporal response or enhance the viability of the embryo or oocyte. For instance, a force that is too large may reduce the viability of an embryo or oocyte, or even destroy them. A force that is too small may not provoke enough temporal response for the purpose of deriving meaningful measurements. Such information can be obtained by experimental testing.

For a human embryo or oocyte, it is determined that when a positive or negative pressure is applied, the suitable range of pressure is between about 0.3 psi and about 1 psi (or between about −0.3 psi and about −1 psi for a negative pressure). In some aspects, the pressure is at least about 0.4, about 0.5, about 0.6 or about 0.7 psi (likewise for negative pressure). In some aspects, the pressure is not higher than about 1, about 0.9, about 0.8, about 0.7, about 0.6, or about 0.5 psi. (likewise for negative pressure). In some aspects, the human embryo suitable for such a pressure is about 1 day, about 2 days or about 3 days following fertilization.

In some aspects, it is contemplated that when a mechanical stimulus is applied, for instance, by applying a pressure, which can be positive or negative, the pressure is maintained at a substantially constant level. This can be helpful to facilitate recording and determination of the temporal response exhibited by the embryo or oocyte. As used herein, the term "substantially constant pressure" means that the pressure is maintained at a level for a desired period of time such that the maximum variation (i.e., difference between the maximum pressure or the minimum pressure and the average pressure) does not exceed about 20%, or alternatively about 15%, or alternatively about 10%, or about 5% of the average pressure.

Also for a human embryo or oocyte, the suitable size of the area on which the mechanical stimulus is applied can be determined experimentally. For a human embryo, the size of the surface area can be between about 25 μm and about 100 μm in diameter. In some aspects, the size is at least about 30 μm, 35 μm, 40 μm, 45 μm, 50 μm, 55 μm, or 60 μm. In some aspects, the size is not larger than about 100 μm, 95, μm, 90 μm, 85 μm, 80 μm, 75 μm, 70 μm, 65 μm, 60 μm, 55 μm, or 50 μm. In some aspects, the size of the surface area can correspond to the internal diameter of a pipette used to generate the mechanical stimulus.

Measurement Methods

In one embodiment, the measurement can be carried out with simple light microscopy. In this respect, a high frame rate can be used to capture detailed time-response curves of the embryo or the oocyte and its contents as it responds to the mechanical stimuli. Based on such images, static and dynamic mechanical parameters can be measured with the material properties of the instruments providing the stimuli.

In some aspects, ultrasound can be used to observe the movements of the embryo. Mechanical sensors such as MEMS devices or fiber optic sensors such as fiber Bragg gratings, photonic crystal fibers, or fiber optic chemical or pressure sensors can also be used to extract information about forces, vibrations, or texture at various spatial locations. Other properties of the embryo can be measured as a strain gauge. The pressure of the media surrounding the embryo can be determined with conventional pressure sensors. Further, accelerometers can be used to calculate various movements or parameters such as resonant frequency. Moreover, various combinations of these techniques can provide a more complete image of spatial and temporal variations in all of the mechanical properties.

Figure 6A:
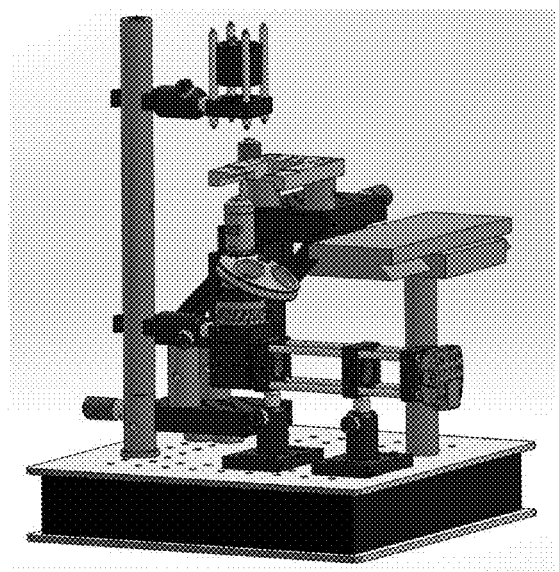
FIG. 6A shows an example setup for applying a mechanical stimulus and detecting a temporal response.
Figure 6B:
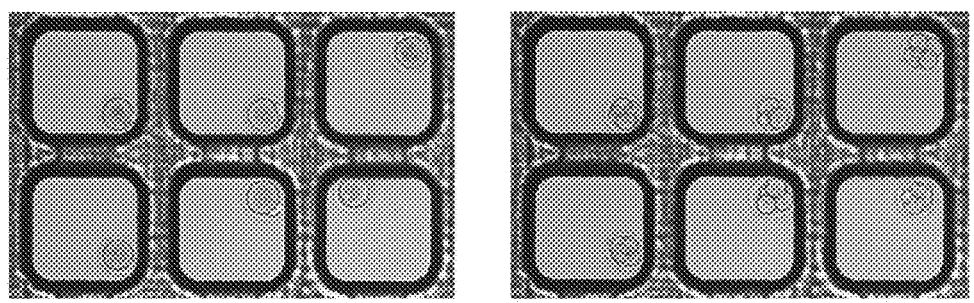
FIG. 6B shows a microwell plate useful for carrying out the mechanical manipulation experiment and embryo tracking while maintaining group culture following manipulation.

In some embodiments, the embryos or oocytes are assessed by measuring cell parameters by time-lapse imaging (FIG. 6A). The embryos or oocytes may be cultured in standard culture dishes. Alternatively, the embryos or oocytes may be cultured in custom culture dishes, e.g. custom culture dishes with optical quality micro-wells (see, e.g., FIG. 6B). In such custom culture dishes, each micro-well holds a single embryo/oocyte, and the bottom surface of each micro-well has an optical quality finish such that the entire group of embryos within a single dish can be imaged simultaneously by a single miniature microscope with sufficient resolution to follow the cell mitosis processes. The entire group of micro-wells shares the same media drop in the culture dish, and can also include an outer wall positioned around the micro-wells for stabilizing the media drop, as well as fiducial markers placed near the micro-wells. The hydrophobicity of the surface can be adjusted with plasma etching or another treatment to prevent bubbles from forming in the micro-wells when filled with media. Regardless of whether a standard culture dish or a custom culture dish is utilized, during culture, one or more developing embryos may be cultured in the same culture medium.

Images are acquired over time, and are then analyzed to arrive at measurements of the one or more cellular parameters. Time-lapse imaging may be performed with any computer-controlled microscope that is equipped for digital image storage and analysis, for example, inverted microscopes equipped with heated stages and incubation chambers, or custom built miniature microscope arrays that fit inside a conventional incubator. The array of miniature microscopes allows the concurrent culture of multiple dishes of samples in the same incubator, and is scalable to accommodate multiple channels with no limitations on the minimum time interval between successive image capture. Using multiple microscopes eliminates the need to move the sample, which improves the system accuracy and overall system reliability. The individual microscopes in the incubator can be partially or fully isolated, providing each culture dish with its own controlled environment. This allows dishes to be transferred to and from the imaging stations without disturbing the environment of the other samples.

The imaging system for time-lapse imaging may employ brightfield illumination, darkfield illumination, phase contrast, Hoffman modulation contrast, differential interference contrast, or fluorescence. In some embodiments, darkfield illumination may be used to provide enhanced image contrast for subsequent feature extraction and image analysis. In addition, red or near-infrared light sources may be used to reduce phototoxicity and improve the contrast ratio between cell membranes and the inner portion of the cells.

Images that are acquired may be stored either on a continuous basis, as in live video, or on an intermittent basis, as in time lapse photography, where a subject is repeatedly imaged in a still picture. In some aspects, the time interval between images should be between 0.001 second to 0.1 second in order to capture the geometric changes. In an alternative embodiment, the time interval between images can be varied depending on the type and magnitude of the mechanical stimulus.

For the purposes of IVF, it is considered advantageous that the embryo be transferred to the uterus early in development, e.g. by day 1, day 2 or day 3, i.e. up through the 8-cell stage, to reduce embryo loss due to disadvantages of culture conditions relative to the in vitro environment, and to reduce potential adverse outcomes associated with embryonic arrest, epigenetic errors, or other factors that may disturb embryo viability during culturing. Accordingly, it is preferable that the measurement of the temporal parameters take place within 1 or 2 days of fertilization, although longer periods of analysis, e.g. about 36 hours, about 54 hours, about 60 hours, about 72 hours, about 84 hours, about 96 hours, or more, are also contemplated by the present methods.

Determining Viability from Measurements

As discussed above, one or more parameters may be measured and employed to determine the developmental potential (e.g., viability) of an embryo or oocyte. Without limitation, such parameters include $k_0$, $k_1$, $\tau$ (or $\eta_0$) and $\eta_1$. In some embodiments, a measurement of a single parameter may be sufficient to arrive at a determination of developmental potential. In some embodiments, it may be desirable to employ measurements of more than one parameter, for example, 2 parameters, 3 parameters, or 4 or more parameters. In some embodiments, the two or more parameters include $k_1$ and $\eta_1$. In some embodiments, the three or more parameters include $k_1$, $\tau$ and $\eta_1$.

When one parameter is used, or multiple parameters are used individually, the determination of viability can be made with comparison to a suitable control, or based on comparison among a few embryos or oocytes in a group. As provided, a suitable control can be a particular sample or a virtual sample generated by pooling information from a group of control samples.

For instance, if $k_1$ alone is used, between two embryos, the one with a higher $k_1$ value is more likely to be viable than the other. Alternatively, a pool of embryos, generated under similar conditions and from similar donors, can be used to produce a cutoff $k_1$ value that separates viable embryos from non-viable embryos. Any $k_1$ value that is greater than this cutoff value predicts that the corresponding embryo is likely viable, and any $k_1$ value that is lower than this cutoff value predicts that the corresponding embryo is not likely viable.

In some aspects, a cutoff range can be used, where the range can be generated from a group of known samples. In this respect, for instance, if a value falls within the range, the value predicts that the embryo or oocyte is viable; otherwise, if the value is beyond the range, a prediction that the embryo or oocyte is non-viable can be made.

The determination can also be made without predetermined cutoff values, cutoff ranges, or other types of summary statistical data obtained from reference samples. For instance, the $k_1$ value of a test embryo can be compared to a group of embryos with known $k_1$ values and viabilities. A non-parametric method, such as nearest neighbor, can then readily determine the likelihood of the test embryo to be viable or non-viable based on comparison of these samples. In this respect, the method entails, after measuring the temporal response from a test sample, comparing the measurement of the test sample to a plurality of samples with known viability and measurements of the temporal responses.

Multivariate methods are capable of making such determination with two or more parameters. Such methods include, without limitation, nearest neighbor, random forest, support vector machine, linear or quadratic discriminant analysis and neuron network. In some aspects, visualization, such as principal component analysis, can assist such determination.

In certain embodiments, use of multiple parameters may be desirable as assaying for multiple parameters may provide for greater sensitivity and specificity. By sensitivity it is meant the proportion of actual positives which are correctly identified as being such. This may be depicted mathematically as the number of true positives divided by the sum of number of true positive and number of false negatives.

Thus, in a method in which "positives" are the embryos or oocytes that have good developmental potential, i.e. that will develop into blastocysts, and "negatives" are the embryos or oocytes that have poor developmental potential, i.e. that will not develop into blastocysts, a sensitivity of 100% means that the test recognizes all embryos that will develop into blastocysts as such. In some embodiments, the sensitivity of the assay may be about 70%, 80%, 90%, 95%, 98% or more, e.g. 100%. By specificity it is meant the proportion of negatives which are correctly identified as such. This may be depicted mathematically as the number of true positives divided by the sum of number of true negatives and number of false positives.

Thus, in a method in which positives are the embryos or oocytes that have good developmental potential, i.e. that will develop into blastocysts, and negatives are the embryos or oocytes that have poor developmental potential, i.e. that will not develop into blastocysts, a specificity of 100% means that the test recognizes all embryos that will not develop into blastocysts, i.e. will arrest prior to the blastocyst stage, as such. In some embodiments, the specificity of the assay may be about 70%, 80%, 90%, 95%, 98% or more, e.g. 100%.

In some embodiments, the assessment of an embryo or oocyte includes generating a written report that includes the artisan's assessment of the subject embryo/oocyte, e.g. a "developmental potential assessment", an "assessment of chromosomal abnormalities", etc. Thus, a subject method may further include a step of generating or outputting a report providing the results of such an assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to an assessment arrived at by methods of the disclosure. A subject report can be completely or partially electronically generated. A subject report includes at least an assessment of the developmental potential of the subject embryo or oocyte, an assessment of the probability of the existence of chromosomal abnormalities, etc. A subject report can further include one or more of: 1) information regarding the testing facility; 2) service provider information; 3) subject data; 4) sample data; 5) a detailed assessment report section, providing information relating to how the assessment was arrived at, e.g. a) cell parameter measurements taken, b) reference values employed, if any; and 6) other features.

The report may include a subject data section, including medical history of subjects from which oocytes or oocytes were harvested, patient age, in vitro fertilization cycle characteristics (e.g. fertilization rate, day 3 follicle stimulating hormone (FSH) level), and, when oocytes are harvested, zygote/embryo cohort parameters (e.g. total number of embryos). This subject data may be integrated to improve embryo assessment and/or help determine the optimal number of embryos to transfer. The report may also include administrative subject data (that is, data that are not essential to the assessment of developmental potential) such as information to identify the subject (e.g., name, subject date of birth (DOB), gender, mailing and/or residence address, medical record number (MRN), room and/or bed number in a healthcare facility); insurance information, and the like), the name of the subject's physician or other health professional who ordered the assessment of developmental potential and, if different from the ordering physician, the name of a staff physician who is responsible for the subject's care (e.g., primary care physician).

The report may include a sample data section, which may provide information about the biological sample analyzed in the assessment, such as the type of sample (embryo or oocyte, and stage of oocyte), how the sample was handled (e.g. storage temperature, preparatory protocols) and the date and time collected. Report fields with this information can generally be populated using data entered by the user, some of which may be provided as pre-scripted selections (e.g., using a drop-down menu).

The report may include an assessment report section, which may include information relating to how the assessments/determinations were arrived at as described herein. The interpretive report can include, for example, time-lapse images of the embryo or oocyte being assessed, and/or gene expression results. The assessment portion of the report can optionally also include a recommendation(s) section. For example, where the results indicate good developmental potential of an embryo, the recommendation can include a recommendation that a limited number of embryos be transplanted into the uterus during fertility treatment as recommended in the art.

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a non-transitory computer readable storage medium, e.g., in a computer memory, zip drive, CD, DVD, etc. Aspects of viability determination using one or more parameters can be carried out using computer code or instructions embodied in a non-transitory computer readable storage medium.

It will be readily appreciated that the report can include all or some of the elements above, with the proviso that the report generally includes at least the elements sufficient to provide the analysis requested by the user (e.g., an assessment of developmental potential).

Utility

As discussed above, methods of the disclosure may be used to assess embryos or oocytes to determine their developmental potential. This determination of developmental potential may be used to guide clinical decisions and/or actions. For example, in order to increase pregnancy rates, clinicians often transfer multiple embryos into patients, potentially resulting in multiple pregnancies that pose health risks to both the mother and fetuses. Using results obtained from the methods of the disclosure, the developmental potential of embryos being transferred to develop into fetuses is determined prior to transfer, allowing the practitioner to decide which and how many embryos to transfer so as to maximize the chance of success of a full term pregnancy while minimizing risk.

Assessments made by the present methods may also find use in ranking embryos or oocytes in a group of embryos or oocytes for their developmental potential. For example, in some instances, multiple embryos may be capable of developing into blastocysts, i.e. will have good developmental potential. However, some embryos will be more likely to achieve the blastocysts stage or a higher-quality blastocyst than other, i.e. they will have better developmental potential than other embryos. In such cases, the present methods may be used to rank the embryos in the group. In such methods, one or more parameters for each embryo/oocyte is measured and compared. The parameters are then employed to determine the developmental potential of the embryos or oocytes relative to one another. In some embodiments, the parameter measurements from each of the embryos or oocytes are employed by comparing them directly to one another to determine the developmental potential of the embryos or oocytes. In some embodiments, the parameter measurements from each of the embryos or oocytes are employed by comparing the cell parameter measurements to a parameter measurement from a reference embryo/oocyte to determine the developmental potentials for each embryo/oocyte, and then comparing the determined developmental potentials for each embryo/oocyte to determine the developmental potential of the embryos or oocytes relative to one another. In this way, a practitioner assessing, for example, multiple zygotes/embryos, can choose only the best quality embryos, i.e. those with the best developmental potential, to transfer so as to maximize the chance of success of a full term pregnancy while minimizing risk.

Assessments made by following the methods of the disclosure may also find use in determining the developmental potential of oocytes that are matured in vitro and stem cells that are cultured in vitro. Information on the developmental potential of oocytes obtained by the methods of the disclosure can guide the practitioner's selection of ooctyes to fertilize, resulting in higher probability of success in deriving blastocysts from these oocytes.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of measuring any of the aforementioned cell parameters, where such reagents may include culture plates, culture media, microscopes, imaging software, imaging analysis software, nucleic acid primers, arrays of nucleic acid probes, antibodies, signal producing system reagents, etc., depending on the particular measuring protocol to be performed.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The present disclosure will be understood more readily by reference to the following examples, which are provided by way of illustration and are not intended to be limiting.

Example 1

This example used a micropipette to perform aspiration on mouse embryos with a step pressure input and used a time-lapse imaging system to measure the aspiration depth of a portion of mouse embryos.

Materials and Methods

Micropipettes (40 μm diameter opening) were used to perform aspiration on mouse embryos and oocytes a few hours before and after fertilization (see, e.g., FIG. 2A-B). Mechanical measurements were conducted for the temporal response (i.e., aspiration depth of inflation) generated by the aspiration. Aspiration curves were fitted to a 4-parameter mechanical model, statistical analyses were conducted using student's t-test and chi-square goodness of fit test.

After embryos were measured, they were either placed in the time-lapse imaging system (FIG. 6A) to see if they develop to the blastocyst stage, or placed in the time lapse system for 2 days (until the system predicts viability) and then gene expression analysis was performed. Gene expression analysis was conducted with Fluidigm's single-cell analysis system and qPCR.

These methods were useful in determining correlation between mechanical measurements and viability, and which mechanical measurements are correlated to which gene expression patterns, and which gene expression patterns are correlated to viability.

For mouse oocytes, upon such measurement, they were allowed to undergo IVF and then followed the same procedure as embryos.

This example, in one study, uses survival to blastocyst stage and time-lapse imaging parameters as a measure of viability. This shows which mechanical parameters are predictive of survival to day 5 in culture. Meanwhile, high-throughput, single cell qPCR analysis were conducted on embryos at 1, 2 and 4-cell stages to identify which mechanical parameters or time-lapse parameters are predictive of gene expression patterns associated with high developmental competence.

The different experimental groups tested included:
1. Embryos measured at day 1, left to develop to blast;
2. Embryos measured at day 1, expression profiles at day 1;
3. Embryos measured at day 1, time lapse+expression profiles at day 2;
4. Controls, left to develop to blast;
5. Controls, expression profiles at day 1;
6. Controls, time lapse+expression profiles at day 2.

Results

Figure 7A:
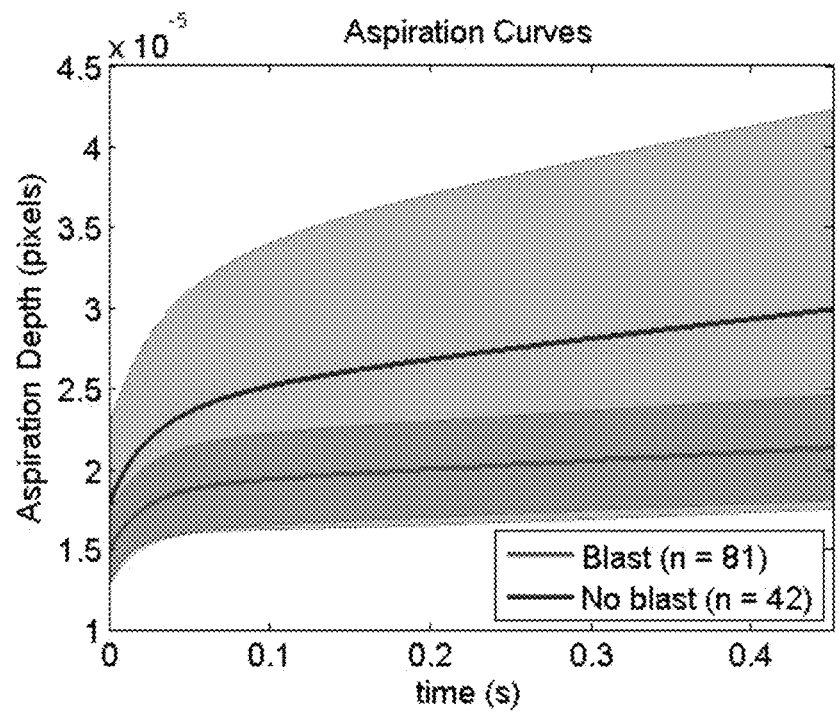
FIG. 7A and FIG. 7B show aspiration curves obtained from a number of embryos in Example 1, correlated to blastocyst survival rates. Asterisks indicate viable embryos.
Figure 7B:
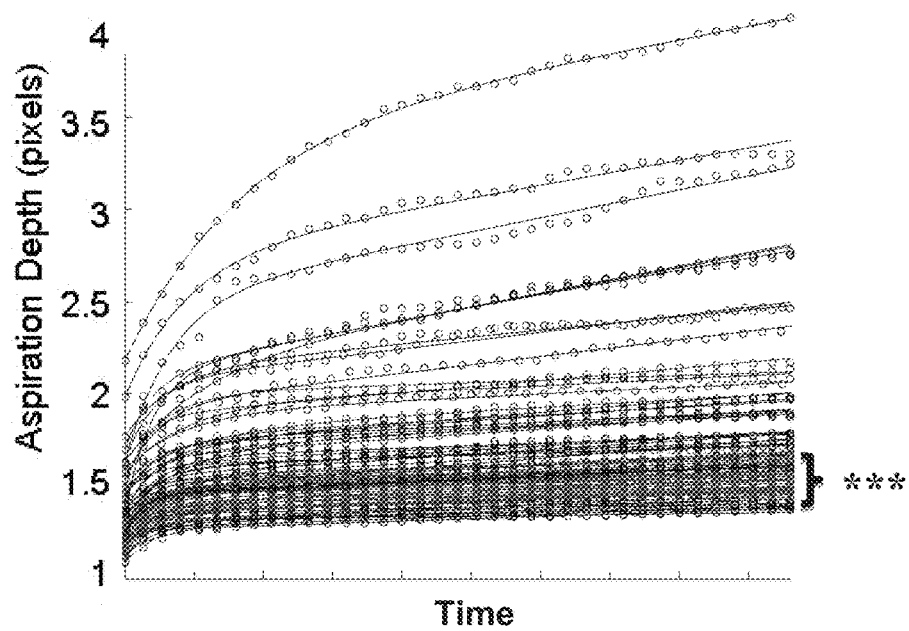

For each sample, an aspiration curve was drawn taking the aspiration depth as y-axis and time as x-axis (FIG. 7B). When all the curves were combined, it is apparent that viable embryos (those that developed into blastocysts) exhibited lower aspiration depth overall and had a more flat curve than the non-viable embryos (compare the shaded areas in FIG. 7A). The asterisks in FIG. 7B indicate a concentrated area where viable embryos are located, whereas the non-viable ones have a more diverse distribution.

Figure 8:
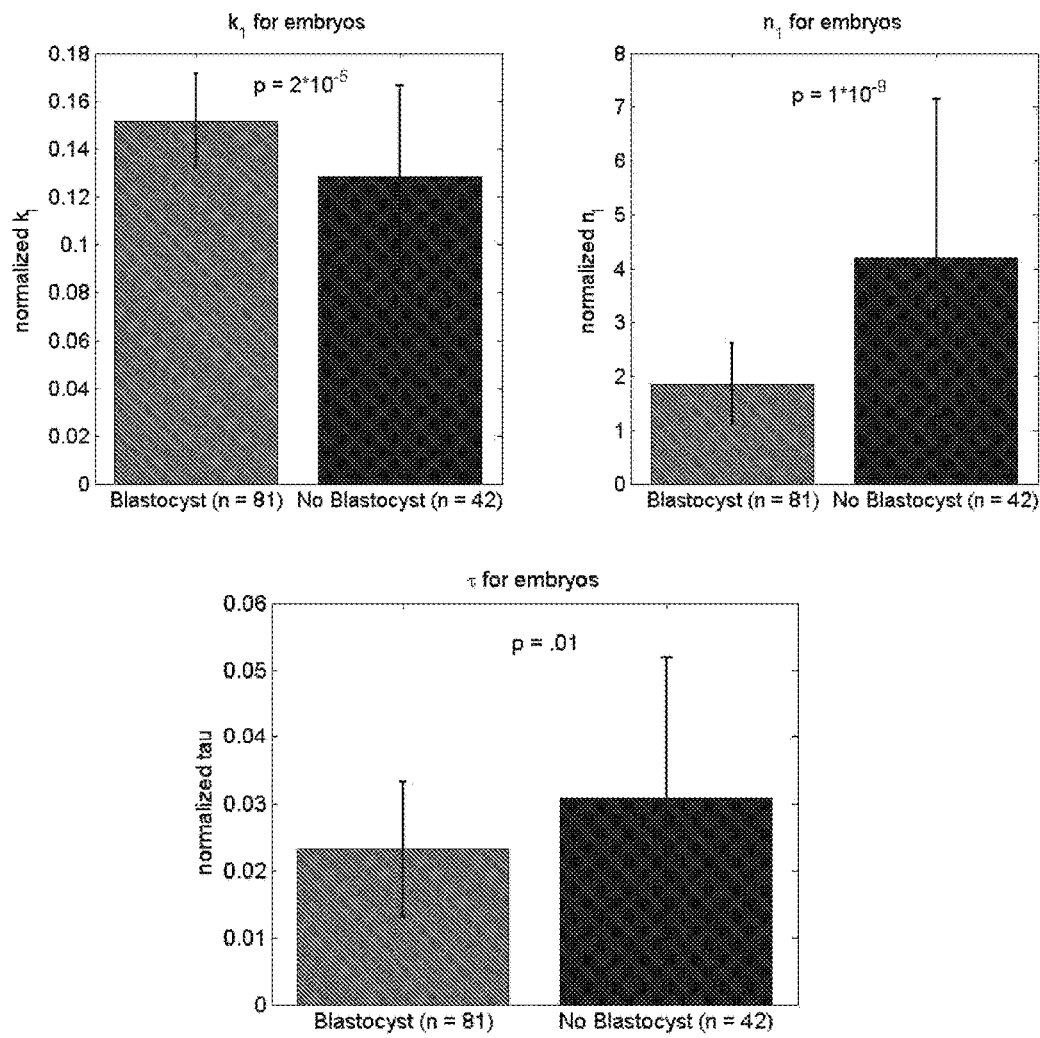
FIG. 8 presents bar charts to show the discrimination power of the parameters, $k_1$, $\eta_1$, and $\tau$.

Each of these aspiration curves was then fitted to a linear elastic solid model with equations (A) and (B) as shown above, and the parameters ($k_0$, $k_1$, $\tau$ and $\eta_1$) were resolved by such fitting. The parameters were then compared among samples. FIG. 8 shows that viable embryos generally have higher $k_1$ values and lower $\eta_1$ and $\tau$ values. Further, as shown in FIG. 8, both of these three parameters, independently, have great discrimination (predictive) power.

Figure 9:
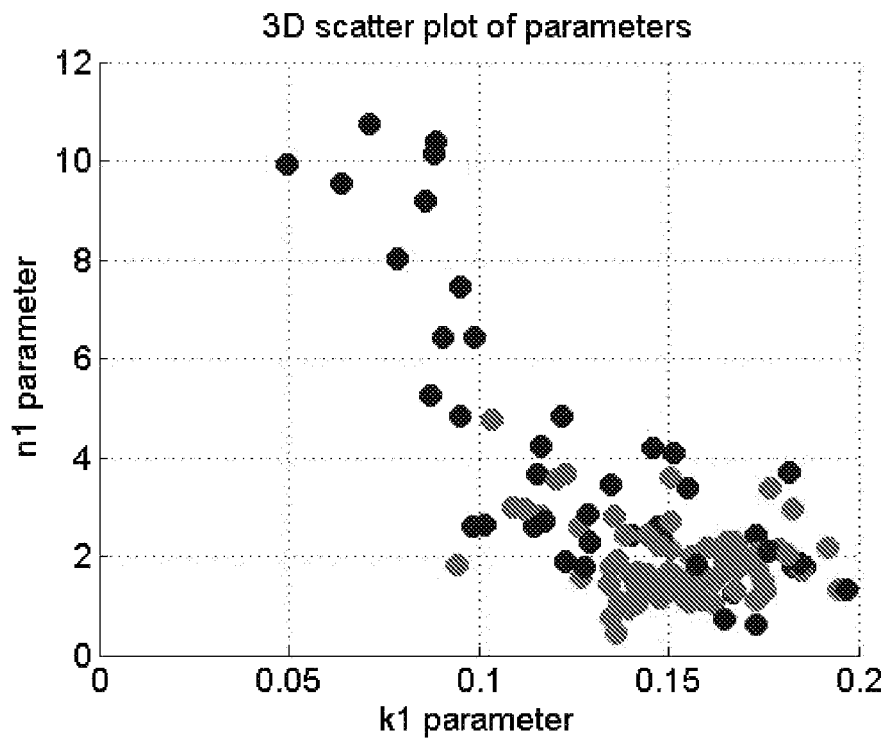
FIG. 9 presents a scatter plot to show that, the combination of parameters, $k_1$ and $\eta_1$, provides even better predictive ability. Light dots represent viable embryos and dark dots represent non-viable embryos.
Figure 10:
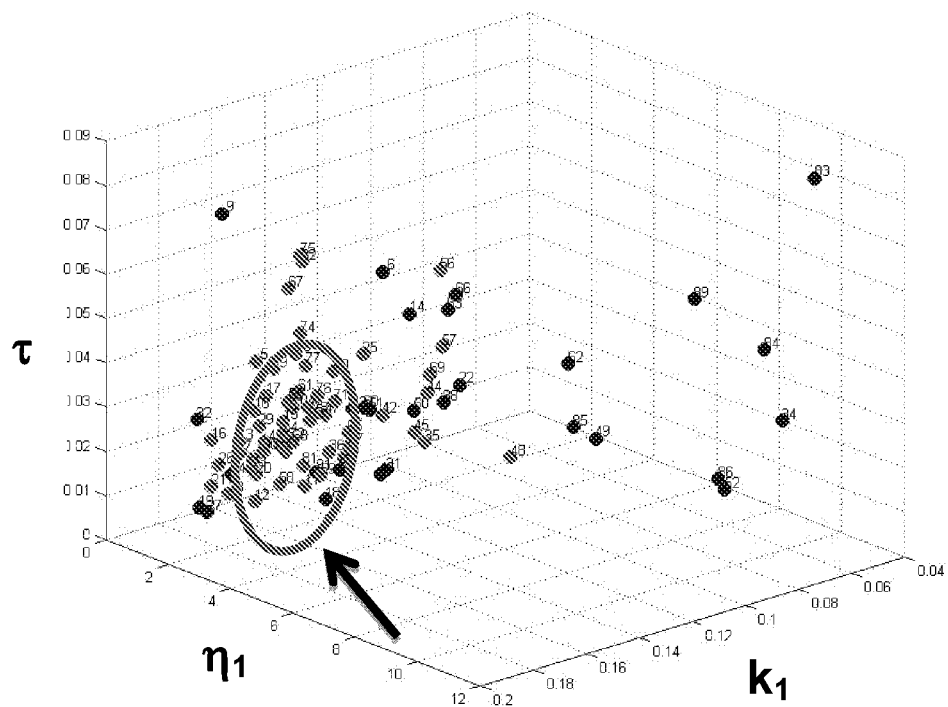
FIG. 10 presents a scatter plot to show that, the combination of parameters, $k_1$ $\tau$, and $\eta_1$, provides even better predictive ability. Light dots represent viable embryos and dark dots represent non-viable embryos. The circle indicates a concentration area where viable embryos are located.

When in combination, $k_1$ and $\eta_1$ showed even greater prediction power. As shown in the scatter plot in FIG. 9, when used together, $k_1$ and $\eta_1$ clearly separate viable embryos from non-viable ones. Still further, when three parameters, $k_1$, $\tau$ and $\eta_1$ are used, the separation is even more clear (FIG. 10).

Figure 11A:
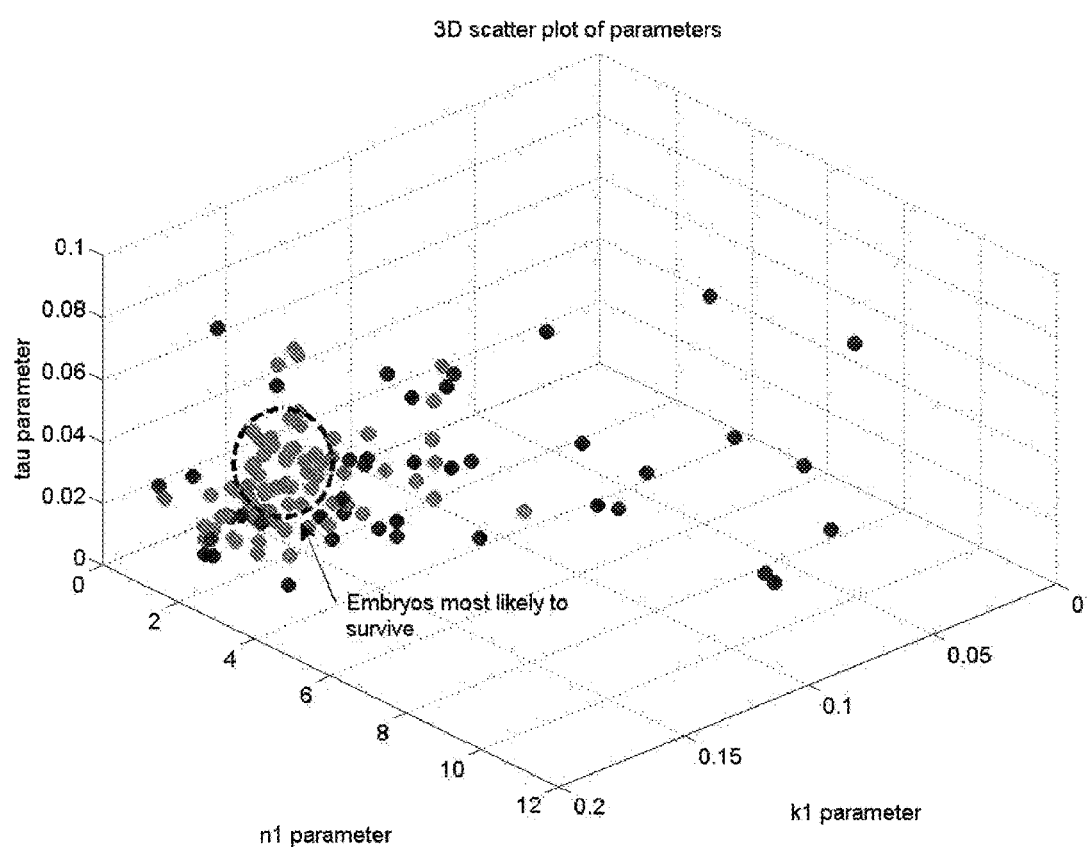
FIG. 11A and FIG. 11B show separation of viable embryos from non-viable embryos on the 3D scatter plot with training (FIG. 11A) and training+testing samples (FIG. 11B)

The predicative power of these parameters was tested by dividing the sample set into a training set (70% samples) and a testing set (30% samples). An elliptical region on a 3D scatter plot was selected to best separate the viable embryos from non-viable embryos. For the purpose of this study, the selection was made to maximize specificity. As shown in FIG. 11A, the specificity of the elliptical region was 100%. The sensitivity, meanwhile, was as high as 41.8%.

Figure 11B:
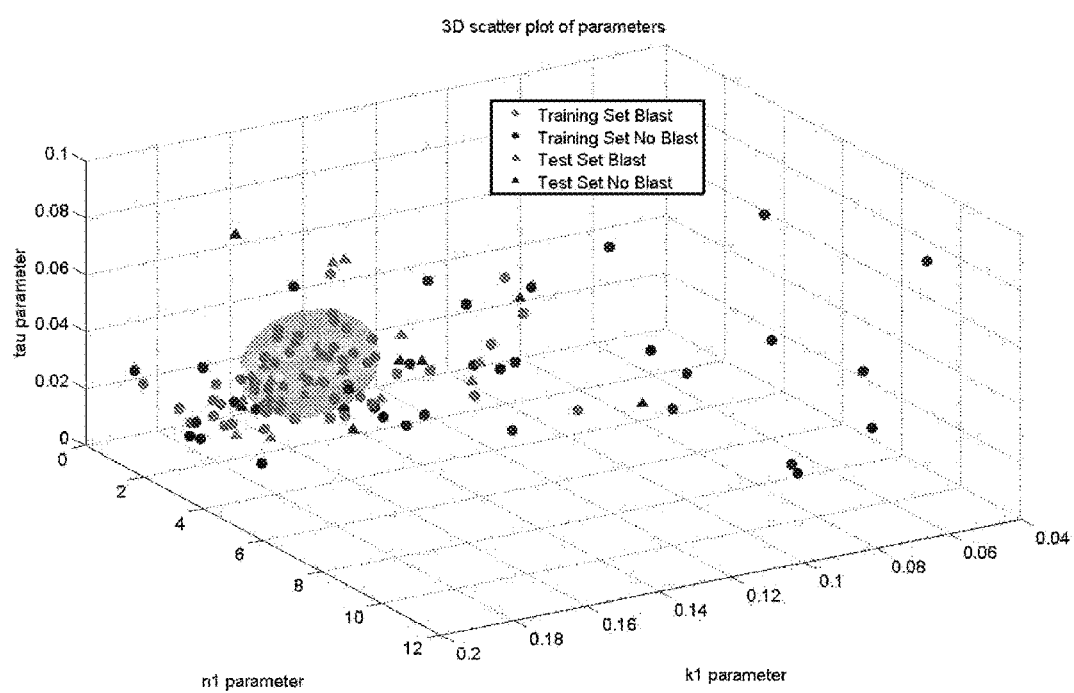

When the elliptical region was applied to the testing set, a 100% specificity was also obtained, while the sensitivity remained at 42.3% (FIG. 11B), confirming the predicative power of these parameters, with respect to viability of the embryos.

Figure 12:
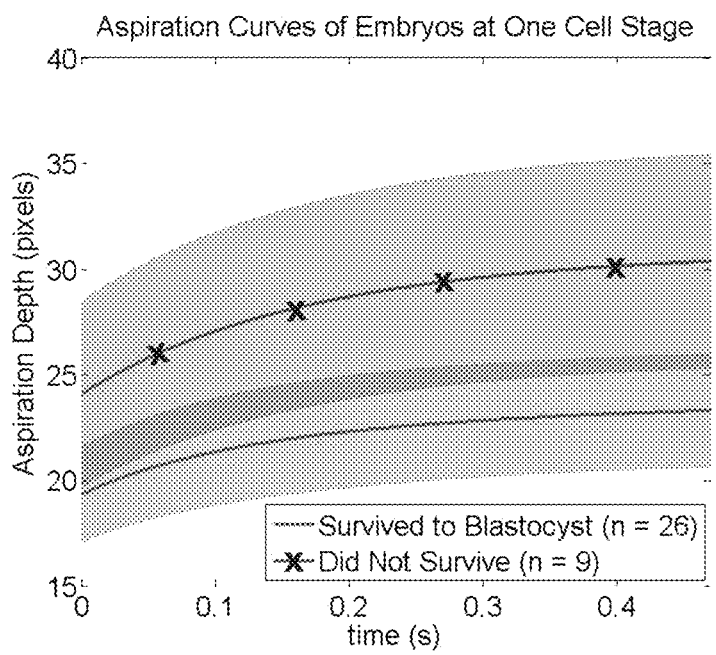
FIG. 12 presents aspiration curves from embryos at one-cell stage.

The same comparison is shown in FIG. 12 for embryos measured at the one-cell stage, indicating that the same method can be predictive in early stage embryos.

Figure 13:
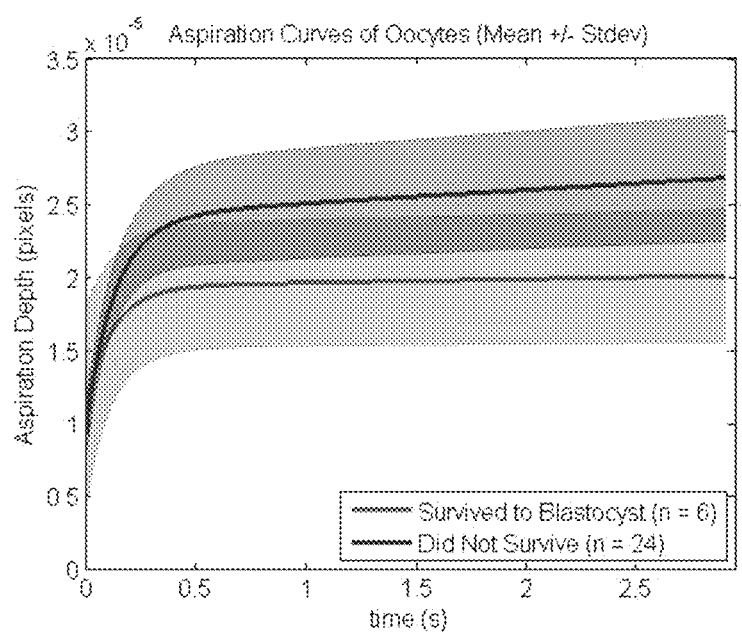
FIG. 13 presents aspiration curves from oocytes.
Figure 14:
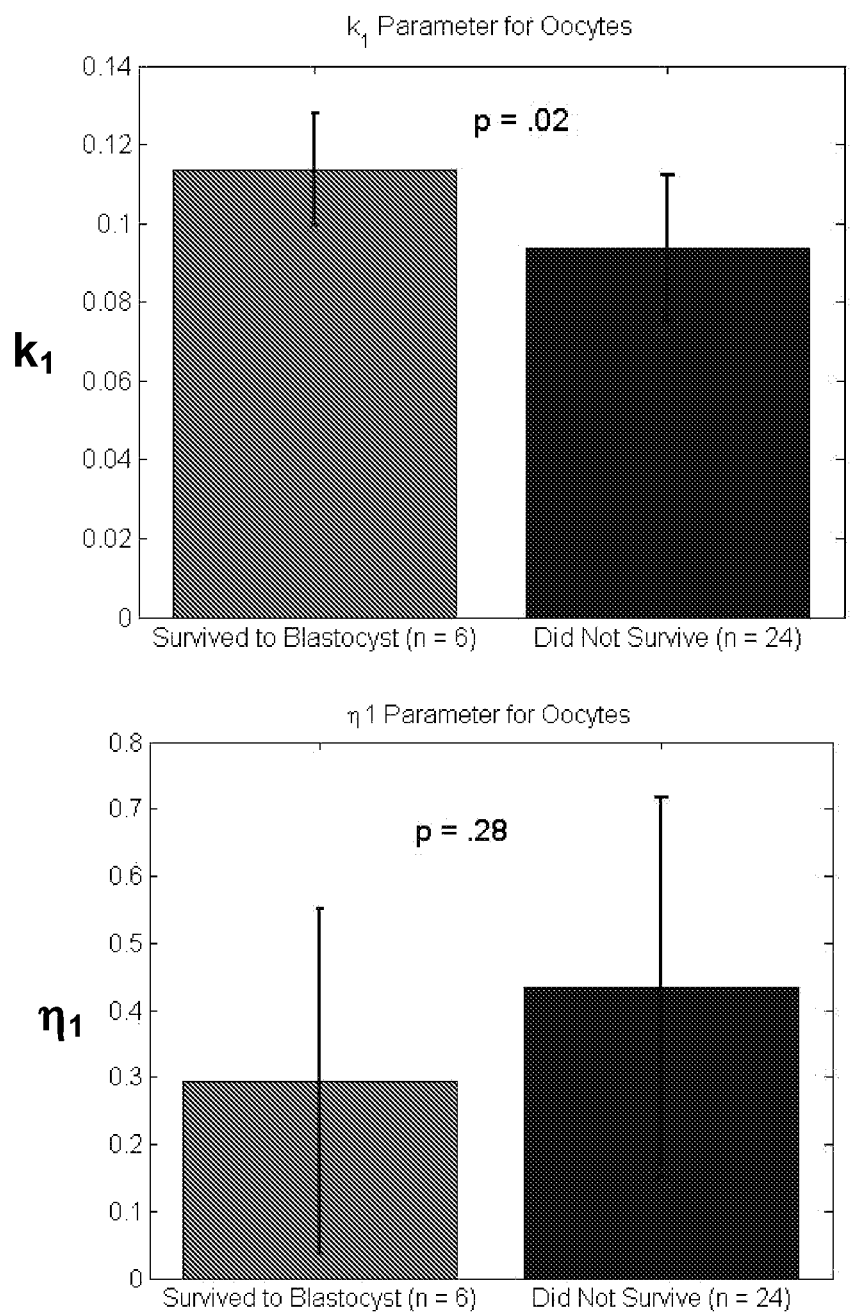
FIG. 14 presents bar charts to show the discrimination power of the parameters, $k_1$ and $\eta_1$, for oocytes.
Figure 15:
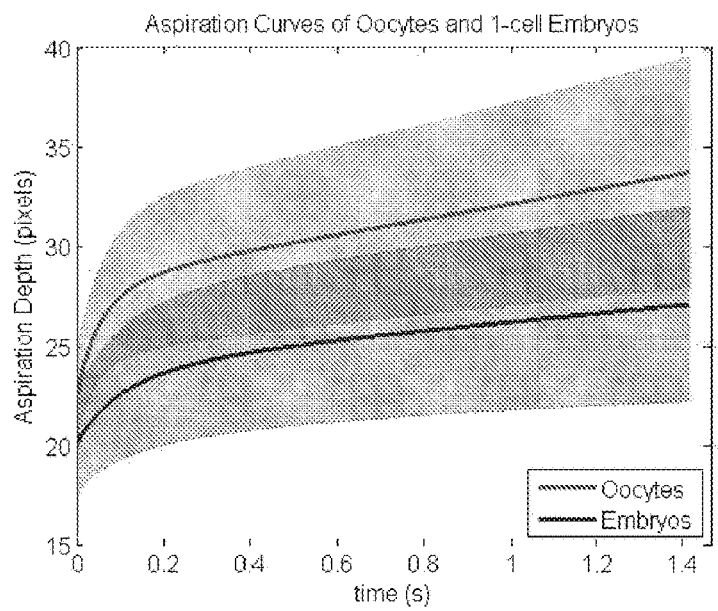
FIG. 15 shows that oocytes, in general, have higher and more steep curves than embryos.
Figure 16:
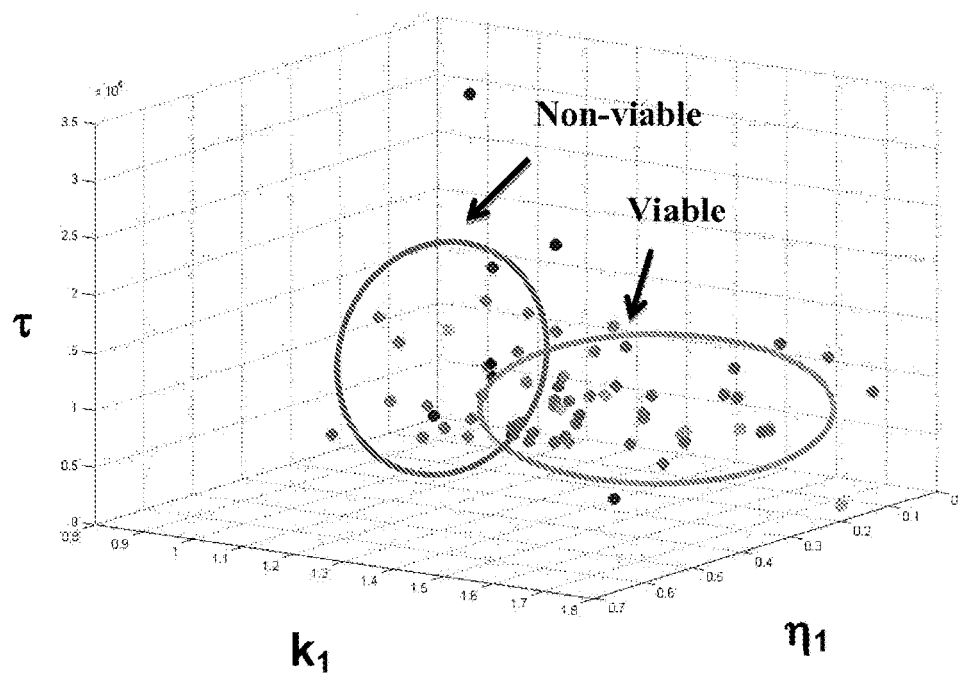
FIG. 16 shows that, despite the difference between oocytes and embryos, viable oocytes and embryos can readily be separated from non-viable oocytes and embryos.

What is more interesting, and surprising as well, is that the same parameters can be used to distinguish oocytes that fertilized into viable embryos from those that did not (FIGS. 13 and 14). Nevertheless, it was observed that oocytes, in general, had lower stiffness than embryos (FIG. 15) suggesting that the cutoff values for oocytes should be tuned from those obtained from embryos. Even without tuning, however, good distinction can be made with these parameters with mixed sample (FIG. 16), showing the great predictive power of these parameters.

Figure 17:
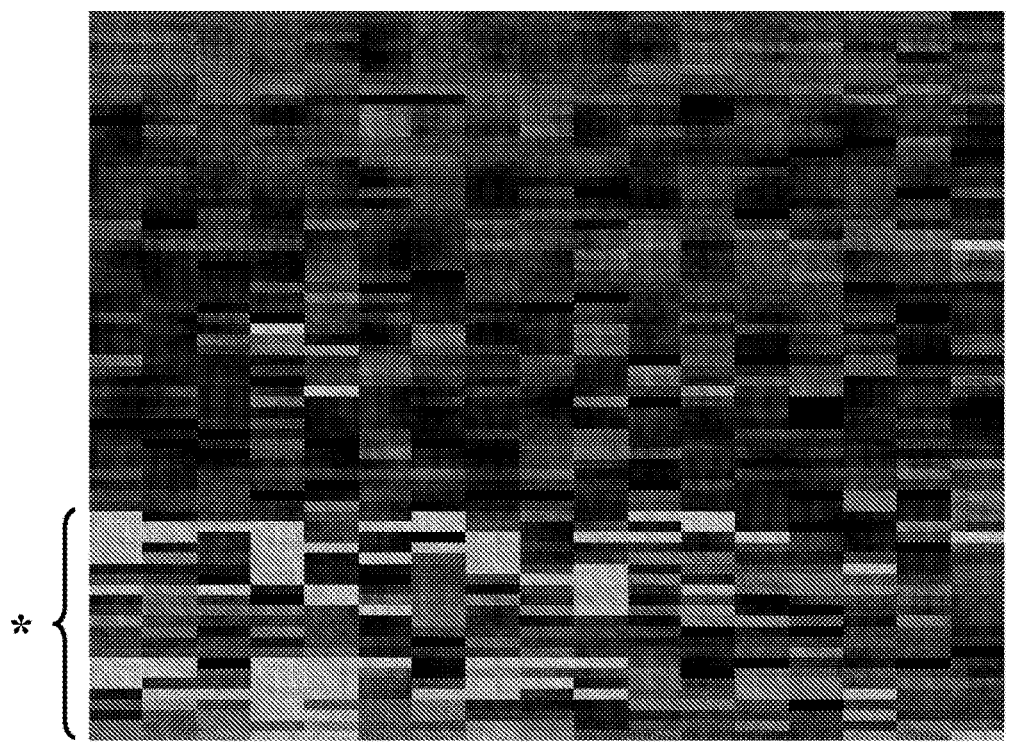
FIG. 17 shows an example heat map of expression profiling with the asterisk indicating a cluster of genes.

For all these experiments, the predicative accuracy can be further assessed with gene expression assay and analysis. It is contemplated that expression changes of the tested genes can be profiled, as illustrated as a heat map in FIG. 17. In the heat map, for instance, a group of genes (indicated by an asterisk) are co-clustered, suggesting that they are co-regulated in a pathway. Gene ontology study of the pathway, it is further contemplated, can suggest that the pathway is related to viability of the embryo. Therefore, such a gene expression profiling analysis can be used to and is expected to validate the parameters.

From these experiments, it was also observed that embryos that received the aspiration, in general, showed improved viability relative to those that did not receive the aspiration. Therefore, it was an unexpected finding that such mechanical manipulation is beneficial to embryo development and has clinical implications.

Moreover, the tables below summarize the findings from different experiment groups, and suggest that the size of the pipette and the magnitude of the pressure can also affect the prediction accuracy and evaluation of the values of the parameters.

30 Um Pipette, 0.7 psi Pressure:

|  | Date | | | | |
| --- | --- | --- | --- | --- | --- |
|  | 6/21 | 6/27 | 7/12 | 7/26 | Totals |
| Control Group (Lived) | 3/6 (50%) | 2/5 (40%) | 6/8 (75%) | 6/10 (60%) | 17/29 (59%) |
| Experimental Group (Lived) | 10/16 (63%) | 7/13 (54%) | 17/19 (89%) | 16/20 (80%) | 50/68 (74%) |

40 um Pipette, 0.2 psi Pressure:

|  | Date | | | |
| --- | --- | --- | --- | --- |
|  | 10/15 | 11/1 | 11/5 | Totals |
| Control Group (Lived) | 4/6 (66%) | 5/6 (83%) | 5/6 (83%) | 14/18 (78%) |
| Experimental Group (Lived) | 13/15 (87%) | 14/15 (93%) | 13/15 (87%) | 40/45 (89%) |

40 um Pipette, 0.4 psi Pressure:

|  | Date 11/30 | Totals |
| --- | --- | --- |
| Control Group (Lived) | 28/43 (65%) | 28/43 (65%) |
| Experimental Group (Lived) | 23/35 (66%) | 23/35 (66%) |

In summary, this example shows that mechanical measurements right before and after fertilization can be used as a biomarker for embryo viability and cytoplasmic maturation.

This example deals mostly with deriving information about the zona pellucida which forms relatively early in development. Still, early deficiencies in proper gene expression can cause the embryo to have compromised developmental competence later on, so that is why the measurement can be indicative or predictive of viability. The mechanical properties of the oocyte or embryo also influence the aspiration curves, even though this example was aspirating from the outside and obtained information mostly about the zona pellucida.

This study will lead to a good predictor of viability, which will give clinicians the information to pick a single embryo to implant if many are viable, or how many to implant if all have low viability. It also provides interesting insight about how a cell's outer mechanical properties are indicative of its functioning on a molecular scale, as well as how mechanical stimuli can influence a cell's function or possibly rescue a dying cell.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

The invention claimed is:

1. A method for selecting a mammalian oocyte for fertilization, comprising:
   performing aspiration on a portion of a surface of the oocyte to inflate the oocyte;
   detecting a temporal response of the oocyte to the aspiration using a microscope, the temporal response including aspiration depths of the oocyte as a function of time while the oocyte is undergoing inflation;
   deriving multiple parameters from the temporal response, the multiple parameters including an elastic parameter and a viscous parameter; and
   based on the multiple parameters, selecting the oocyte for fertilization.

2. The method of claim 1, wherein deriving the multiple parameters includes fitting the aspiration depths to a viscoelastic model.

3. The method of claim 2, wherein the viscoelastic model is represented as a combination of multiple elastic components and multiple viscous components.

4. The method of claim 1, wherein detecting the temporal response is performed over a time period including 5 seconds from initiation of the aspiration.

5. The method of claim 1, wherein detecting the temporal response is performed over a time period including 0.5 second from initiation of the aspiration.

6. A method for selecting a human embryo for transfer to a human subject, comprising:
   performing aspiration on a portion of the human embryo to inflate the human embryo;
   detecting a temporal response of the human embryo to the aspiration using a microscope, the temporal response including aspiration depths of the human embryo as a function of time while the human embryo is undergoing inflation;

deriving multiple parameters from the temporal response, the multiple parameters including an elastic parameter and a viscous parameter, the multiple parameters being indicative of viability; and selecting the human embryo, according to the multiple parameters, for transfer to the human subject.

7. The method of claim 6, further comprising transferring the human embryo to the human subject.

8. The method of claim 6, wherein deriving the multiple parameters includes fitting the aspiration depths to a viscoelastic model.

9. The method of claim 7, wherein the viscoelastic model is represented as a combination of multiple elastic components and multiple viscous components.

10. The method of claim 6, wherein the human embryo is at or less than 1 day old following fertilization.

11. The method of claim 6, wherein detecting the temporal response is performed over a time period including 5 seconds from initiation of the aspiration.

12. The method of claim 6, wherein detecting the temporal response is performed over a time period including 0.5 second from initiation of the aspiration.

13. A method for selecting a human oocyte from a plurality of human oocytes for fertilization, comprising:

for each human oocyte of the plurality of human oocytes,
applying a mechanical stimulus to the human oocyte to deform the human oocyte;
detecting a temporal response of the human oocyte to the mechanical stimulus, the temporal response including geometric change of the human oocyte as a function of time while the human oocyte is undergoing deformation; and
deriving an elastic parameter and a viscous parameter of the human oocyte from the temporal response; and
based on the elastic parameter and the viscous parameter, selecting the human oocyte from the plurality of human oocytes for fertilization.

14. The method of claim 13, wherein applying the mechanical stimulus includes inflating a portion of each human oocyte of the plurality of human oocytes through an opening.

15. The method of claim 13, further comprising fertilizing the selected human oocyte.

16. A method for selecting a mammalian embryo for transfer to a mammalian subject, comprising:

obtaining images of the embryo while the embryo is undergoing inflation by aspiration;
detecting a temporal response of the embryo to the aspiration from the images, the temporal response including aspiration depths of the embryo as a function of time while the embryo is undergoing inflation;
deriving multiple parameters from the temporal response, the multiple parameters including an elastic parameter and a viscous parameter; and
based on the multiple parameters, selecting the embryo for transfer to the mammalian subject.

17. The method of claim 16, wherein deriving the multiple parameters includes fitting the aspiration depths to a viscoelastic model.

18. The method of claim 17, wherein the viscoelastic model is represented as a combination of multiple elastic components and multiple viscous components.

* * * * *